United States Patent
Munekane

(10) Patent No.: US 7,511,269 B2
(45) Date of Patent: Mar. 31, 2009

(54) METHOD OF APPROACHING PROBE AND APPARATUS FOR REALIZING THE SAME

(75) Inventor: Masanao Munekane, Chiba (JP)

(73) Assignee: SII NanoTechnology Inc. (JP)

( * ) Notice: Subject to any disclaimer, the term of this patent is extended or adjusted under 35 U.S.C. 154(b) by 481 days.

(21) Appl. No.: 11/208,830

(22) Filed: Aug. 22, 2005

(65) Prior Publication Data
US 2006/0043287 A1 Mar. 2, 2006

(30) Foreign Application Priority Data
Aug. 25, 2004 (JP) ............................ 2004-245238
Jun. 30, 2005 (JP) ............................ 2005-190941

(51) Int. Cl.
*G01N 23/00* (2006.01)
(52) U.S. Cl. ................. 250/307; 250/306; 250/309; 250/311; 324/756; 324/758; 324/754; 977/851; 977/881
(58) Field of Classification Search ............... 250/307, 250/306, 309, 311; 324/756, 758, 754; 977/851, 977/881
See application file for complete search history.

(56) References Cited

U.S. PATENT DOCUMENTS

2003/0184332 A1* 10/2003 Tomimatsu et al. ......... 324/756
2008/0258056 A1* 10/2008 Zaykova-Feldman et al. .... 250/307

FOREIGN PATENT DOCUMENTS

JP 2001235321 A * 8/2001

* cited by examiner

*Primary Examiner*—Jack I Berman
*Assistant Examiner*—Michael Maskell
(74) *Attorney, Agent, or Firm*—Adams & Wilks

(57) ABSTRACT

A method of approaching a probe to a target position on a sample mounted on a sample stage tilted at a preselected tilt angle about a tilt axis of the sample stage. A distance between the tip of the probe and the target position of the sample is observed with a charged particle beam microscope while approaching the tip of the probe to the target position on the sample. The probe is moved in a direction so that on a display of the charged particle beam microscope, the tip of the probe and the tip of a shadow of the probe on the sample coincide at the target position on the sample.

15 Claims, 6 Drawing Sheets

METHOD OF APPROACHING PROBE AND APPARATUS FOR REALIZING THE SAME

BACKGROUND OF THE INVENTION

The present invention relates to a method of approaching a probe to a specified place of a sample in a focused microscope or an electron microscope, and to an apparatus for realizing the same.

In the focused microscope or the electron microscope, there is occasionally required an operation for approaching the probe to the specified place of the sample. For example, in a case where, by using a focused ion beam (FIB) apparatus, a minute sample is cut off from the sample such as a wafer and picked up by the probe, it is necessary to confirm whether or not the minute sample has been completely cut off from a sample main body. Further, also when, in order to measure electrical characteristics in a predetermined place of the sample such as a semiconductor device, a manipulator to which the probe has been attached is driven under microscope observation, a needle-like probe tip is directly contacted to an observed portion and the electrical characteristics of the above portion are measured by sending an electric current to a sample piece, there are required confirmations of an approach and a contact of that probe with the observed portion. As a method of confirming that contact, hitherto since a judgement of the contact has been performed by a worker by visually observing a microscope image depicted on a monitor, a detection has been vague. For example, notwithstanding the fact that a portion becoming the sample for a transmission electron microscope (TEM) contacts with a tip part of the probe, there has occasionally existed a case where the confirmation or the detection by the microscope image has been delayed, and such an inconvenience has resulted in that, by such a delay of the detection, the sample for the TEM and a contacting terminal of the probe have been injured by the tip part of the probe. Whereupon as a method of certainly detecting the contact, there is presented such a method that, if a probe voltage is beforehand applied to the probe and, while operating a micro-actuator while microscope-observing it, the probe attached to its tip part is approached to the minute sample to thereby cause a tip of the probe to contact to the sample, since a voltage level changes, this change is made a contact detection signal.

In Patent Document 1, there is disclosed "a focused ion beam apparatus" whose object is to provide an FIB apparatus capable of certainly detecting the contact concerned without providing a new electric source in order to detect the contact between the probe and the sample. As shown in FIG. 6, a probe 1 of this FIB apparatus 101 is grounded through an ammeter 12. When the probe 1 and a sample 5 are being approached by a control of a drive unit 22, an FIB from an FIB barrel 10 is irradiated to the sample 5. At this time, in a case where the probe 1 is not contacting with the sample 5, an electric current generated in the sample 5 by the irradiation of the FIB flows toward an inside of the sample 5. In contrast to this, in a case where the probe 1 is contacting with the sample 5, the electric current generated in the sample 5 flows toward the probe 1. At a point in time at which the probe 1 has contacted with the sample 5, the electric current flowing through the probe 1 increases. It is one in which, by monitoring the electric current flowing through the probe 1 by the ammeter 12, the contact between the probe 1 and the sample 5 is detected from a change quantity of the electric current concerned. That is, it becomes a work in which an operation of the approach is performed while microscope-observing, and the contact is detected by the electric current value change in the ammeter.

Further, as a contact detecting method of the probe, there is presented also a method in which a displacement of a piezoelectric element is monitored as shown in Patent Document 2. For example, in the Patent Document 2, there are presented "a probe unit and a sample operating apparatus using the same" whose object in each is to provide a sample making apparatus or a failure detecting apparatus, which possesses an inexpensive detecting means capable of detecting the contact between the sample and an explorer irrespective of a kind of the sample. This apparatus is one possessing a probe unit in which the explorer which comprises a needle-like electrically conductive material and whose tip has an acute angle shape is fastened to a free end of a strain detecting beam having a piezo-resistance layer whose resistance value changes in compliance with its own displacement, and the other end of the strain detecting beam is retained to a fixed base functioning also as a foundation of the strain detecting beam provided with a conductor part having a current-carrying function for the piezo-resistance layer and the explorer. In this apparatus, there is adopted such a contact detecting method that, if the explorer contacts with the sample, the explorer transmits a strain amount as its reaction to the strain detecting beam and, by the fact that its resistance value has changed, a contact detecting circuit judges the contact between the explorer and the sample. In this method, the operation of the approach is performed while microscope-observing, and the contact is detected by the electric current value change in the ammeter.

Additionally, in Patent Document 3, there are disclosed "a probe driving method and a probe apparatus" whose object in each is to cause the probe to safely and efficiently contact a sample surface by monitoring a probe height. The probe driving method shown in this Document goes through a process in which a charged particle beam is irradiated to a sample image containing a probe image obtained by detecting secondary particles or reflected particles discharged by the charged particle beam irradiation, a distance (1st distance) between a tip position of the probe and a specified position on the sample, and a process in which the charged particle beam is irradiated to the sample and the probe from a 2nd angle different from the 1st angle to thereby find, on the sample image containing the probe image obtained by detecting secondary particles or reflected particles discharged by the charged particle beam irradiation, a distance (2nd distance) between the tip position of the probe and the specified position on the sample, and is an approach in which a distance between the sample and the probe is calculated on the basis of the 1st and 2nd angles and the 1st and 2nd distances, and the probe is driven in a direction of the sample in compliance with the calculated distance between the sample and the probe. In a case where the sample surface is electrically floating, a luminance becomes low due to an electrification by an ion beam irradiation, and the contact can be detected because, if the electrically conductive probe contacts, the charge is dissolved and the image becomes bright. Further, in this Document, there is a description about a method in which a shadow, of the probe, occurring just before contacting to the sample is detected from slightly above beyond the probe, thereby foreseeing an approaching state from a change in contrast.

[Patent Document 1] JP-A-2001-235321 Gazette "FOCUSED ION BEAM APPARATUS, CONTROLLING METHOD OF FOCUSED ION BEAM APPARATUS AND CONTACT DETECTING METHOD", Laid-Open on Aug. 31, 2001

[Patent Document 2] JP-A-2002-33366 Gazette "PROBE UNIT AND SAMPLE OPERATING APPARATUS USING THE SAME", Laid-Open on Jan. 31, 2002

[Patent Document 3] JP-A-2002-40107 Gazette "PROBE DRIVING METHOD AND PROBE APPARATUS", Laid-Open on Feb. 6, 2002

Since the conventional contact detecting method mentioned above is one utilizing a physical phenomenon, such as electrical change or piezoelectric phenomenon, occurring as a result of the contact, it is difficult to cause the probe to approach the sample so as to softly contact therewith while observing. Further, in a case of the electrical change, in a case where a contact object is an insulator, the detection cannot be performed. Also as to an electrically conductive material, there is a case where electrical characteristics are difficult to be obtained because an oxide film is formed on its surface.

Objects of the present invention are to provide a method in which the probe can approach the minute sample so as to certainly and softly contact the sample only by operating the manipulator while microscope-observing without requiring a special detection means, and to provide an apparatus for implementing the same.

SUMMARY OF THE INVENTION

A method of approaching a probe of the present invention has been adapted such that, when a distance between a probe tip and a target position of the sample position to be contacted decreases while observing a micro-order level distance between them, the probe is moved in a direction such that, while observing a shadow of the probe by a charged particle beam microscope, appearing in the microscope picture, tip parts of the probe and the shadow of the probe coincide at a position made a contact target on an observation image. A method of approaching a probe of the present invention has been adapted such that a direction and a distance of the sample position to be contacted to the probe position are calculated from a relative distance measured value in plural microscope images photographed at two or more different known tilt angles and a data of the tilt angles and, on the basis of it, a movement of the probe is performed such that the distance between the probe and the sample position to be contacted becomes several microns or less.

This shadow of the probe is a phenomenon occurring because, if the probe approaches a surface of the sample at an oblique observation time, arrivals of secondary electrons (or secondary ions) generated from the sample surface in the vicinity of the probe to a detector are shielded, and it becomes more noticeable the more a distance between the probe and the sample surface is near and narrow. Also the fact that, when a secondary electron image of a minute hole is observed by an electron microscope, an inside of the hole seems dark in comparison with an outside is similarly due to the shielding when the secondary electrons emerge from the inside of the hole.

A more desirable method of approaching a probe of the present invention comprises a step of position-coinciding, under a state that a tilt axis of a sample stage and a height position of a sample surface are coincided, a sample position to be contacted and a probe tip part position on a microscope image plane in which a charged particle beam has been irradiated from a sample surface vertical direction, a step of measuring a relative distance between the sample position to be contacted and the probe tip part position in a microscope image photographed with the sample stage being tilted by a predetermined angle, a step of calculating, from a data of the relative distance and the tilt angle, a distance between both, a step of moving the probe in a direction of a contact object, and a step of moving it in the same direction till tip parts of the probe and a shadow of the probe coincide while microscope-observing.

A method of approaching a probe of the present invention has been adapted such that, by applying to the probe a voltage of a frequency of such a degree that a luminance change can be visually observed to change a detection quantity of second electrons and second ions during observation by the charged particle beam microscope, the shadow of the probe is luminance-changed. At this time, a constant voltage can be used for the voltage applied to the probe rather than a frequency voltage.

Further, an apparatus for performing a method of the present invention is a charged particle beam apparatus possessing a microscope function, and has been made one in which a micro-manipulator to whose tip part there has been attached a probe formed by an electrically conductive material is monolithically fixed to a stage of four or more drives possessing at least x, y, z axes and a tilt axis, and a variable voltage supplying means is connected to the probe.

Since a method of approaching a probe of the present invention is one having been adapted such that, under a state that is a proximity state in which the distance between the probe and the sample position to be contacted is micro-level, the probe is moved in the known direction, while observing under the proximity state by the microscope the shadow, of the probe, appearing in the charged particle beam microscope picture, till the tip parts of the probe and the shadow of the probe coincide on the observation image plane, it is possible to softly move the probe till it contact to the sample.

Since a method of approaching a probe of the present invention has been adapted such that the direction and the distance of the sample position to be contacted to the probe position are calculated from the relative distance measured value in plural microscope images photographed at different known tilt angles and the data of the tilt angles and, on the basis of it, the movement of the probe is performed such that the distance between the probe and the sample position to be contacted becomes several microns or less, it is possible to certainly catch the shadow of the probe in the microscope picture.

In a more desirable method of approaching a probe of the present invention, by position-coinciding, under the state that the tilt axis of the sample stage and the height position of the sample surface are coincided, the sample position to be contacted and the probe tip part position on the microscope picture in which the charged particle beam has been irradiated from the sample surface vertical direction, it is possible to bring the tip position of the probe to a direction perpendicular to the sample face of the sample position to be contacted, and there is measured the relative distance between the sample position to be contacted and the probe tip part position in the microscope image photographed with the sample stage being tilted by the predetermined angle, so that it is possible to calculate, from the data of the relative distance and the tilt angle, the distance between both. And, on the basis of that calculated distance, by linearly moving the probe till the distance of several microns, it is possible to certainly catch the probe and its shadow in the microscope picture. Additionally, since it has been adapted so as to move it in the same direction till the tip parts of the probe and the shadow of the probe coincide while microscope-observing, it is possible to softly move the probe till it contacts to the sample.

Since a method of approaching a probe of the present invention has been adapted such that, by applying to the probe an arbitrary voltage or the voltage of the frequency of such a degree that the luminance change can be visually observed, the shadow of the probe is luminance-changed, it is possible to certainly catch the shadow of the probe and a work for the approach becomes easy. Even in a case where there are irregularities in the sample surface or there is a figure-like pattern liable to be confounded with the shadow, the shade which luminance-changes can be easily distinguished.

Further, since an apparatus for performing a method of the present invention is the charged particle beam apparatus possessing the microscope function, and has been made one in which the micro-manipulator to whose tip part there has been attached the probe formed by the electrically conductive material is monolithically fixed to the stage of four or more drives possessing at least x, y, z axes and the tilt axis, a positional relation between the probe and the sample is not changed even if the stage is tilted. And, since the variable voltage supplying means is connected to the probe, it is possible to certainly catch the shade of the probe on the microscope image plane by applying a voltage change of a speed capable of discriminating the luminance change.

Figure 1A:
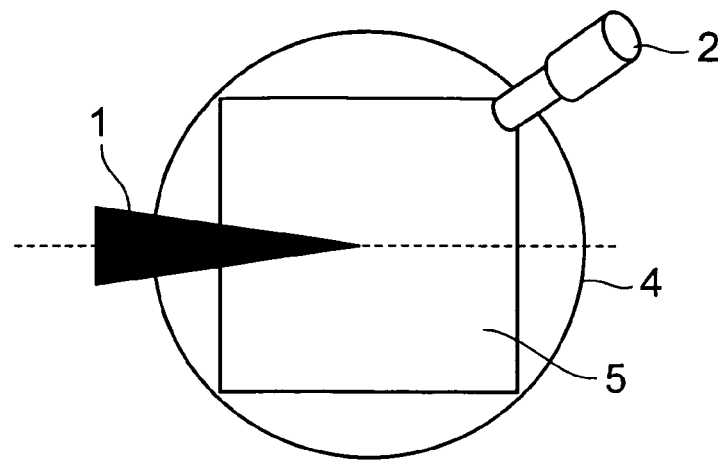
FIGS. 1A-1D are figures explaining a principle of a method, of the present invention, for certainly and softly approaching a probe to a specified position of a minute sample.

DESCRIPTION OF REFERENCE NUMERALS AND SIGN 1 probe
1a shadow of probe
2 secondary charged particle detector
3 micro-manipulator
4 sample stage
5 sample
6 tilt axis
9 variable voltage source
10 charged particle beam lens-barrel
12 ammeter
22 drive unit
101 FIB apparatus
x sample contact position

DETAILED DESCRIPTION OF THE PREFERRED EMBODIMENT

The present invention has started in presenting a method in which the probe can approach to the minute sample so as to certainly and softly contact to it only by operating the manipulator while microscope-observing without requiring a special detecting means such as ammeter, piezoelectric element and sensor. Since the conventional contact detecting method is one utilizing the physical phenomenon, such as electrical change or piezoelectric phenomenon, occurring as the result of the contact, in view of the fact that it is difficult to cause the probe to softly contact to the sample while observing, there has been groped a method of monitoring a state before the contact. It has been known that, if the microscope observation is being performed by the scanning electron microscope (SEM) or the scanning ion microscope (SIM) while scanning the needle-like probe 1, in its microscope image plane there appears a probe shadow 1a like in FIG. 1C or 1D. In the above Patent Document 3, although there is a description that, by detecting this shadow, of the probe, occurring just before the contact to the sample, a state having approached till several μm is foreseen, in the present invention it is an approach method in which, not only by merely foreseeing the state where the probe has approached till several μm to the sample but by more positively utilizing this shadow, i.e., while observing by a charged particle beam microscope set to a tilt angle of several tens degrees, the probe is moved to a sample face such that the probe 1 is caused to coincide with a tip part of the shadow 1a of the probe on an observation image plane.

Figure 1B:
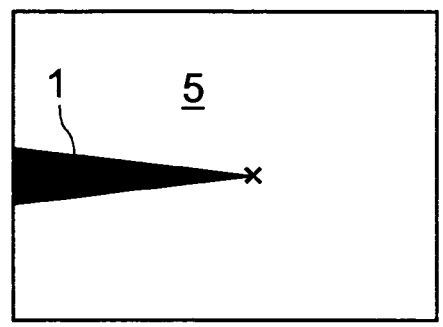
Figure 1C:
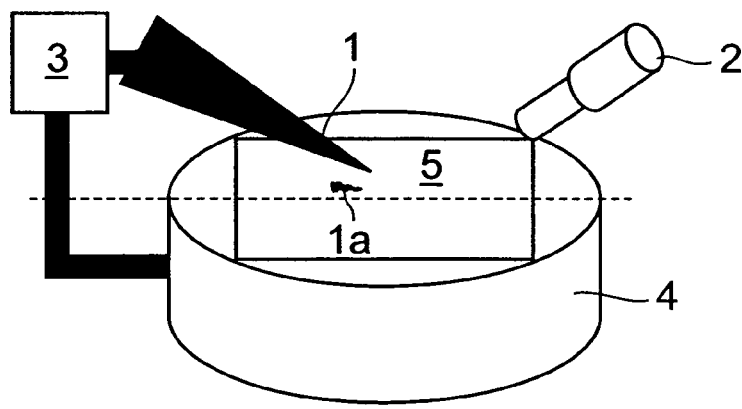

In a case where an interstice exists between a probe 1 tip and a sample 5 surface, if microscope-observed from an oblique direction like in FIG. 1C, a probe 1 tip part and its shadow 1a are always not in contact with each other. Reversely, it the probe tip and the sample face are contacting, they become a contact state also in a microscope image from the oblique direction. If the probe 1 is approached in a sample 5 direction such that the tip of the probe 1 concides with a tip of the shadow 1a while monitoring this microscope image plane, it can be softly and certainly approached.

Figure 2:
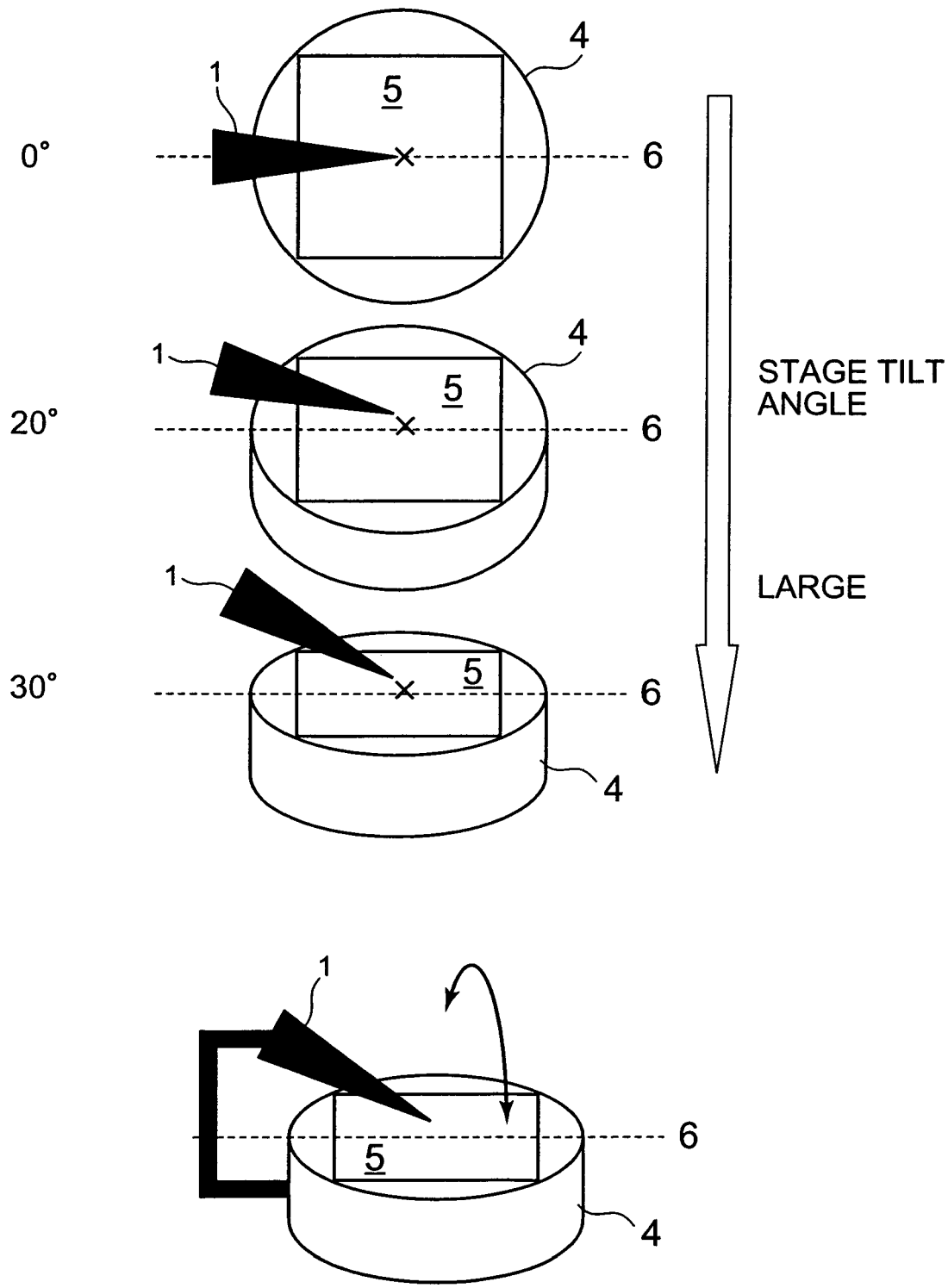
FIG. 2 is a figure explaining a relation, in a microscope image, between a probe position and the specified position of the minute sample.

This shadow of the probe can be observed in the microscope image under a state that the probe has approached to a distance of micro-level from the sample face. For this reason, in the present invention, it is necessary that, first as an initial approach, the probe is brought to a distance of several μm or less from a sample position to be contacted. Whereupon, it is explained how a position of a tip part of the probe 1 and a position x of the sample to be contacted are confirmed in the microscope image. As shown in FIG. 2, depending on an observation direction, i.e., from which direction with respect to a face of a sample stage 4 a charged particle beam is irradiated, its picture becomes changed. Even if the position of the tip part of the probe 1 coincides with the position x of the sample to be contacted when a tilt angle of the stage 4 is 0°, i.e., when the beam is irradiated from a vertical direction with respect to a stage face, it does not necessarily mean that both are contacting. If observed from 20° angle or 30° angle by adjusting the tilt angle, it can be seen that there is an interstice between both. On the basis of two or more microscope pictures photographed at different tilt angles, a distance between both can be calculated from the tilt angle and a relative distance in the picture on that occasion. Incidentally, if the position of the tip part of the probe 1 coincides with the position x of the sample to be contacted in the picture at tilt angle 0°, it means that the tip part of the probe 1 exists just above the position x of the sample to be contacted, i.e., that it is located in a vertical direction with respect to the sample face. Accordingly, a relative distance d between both in the picture obtained by tilting the stage by an angle α from this state becomes a value obtained by multiplying an actual inter-both distance $d_o$ by sin α and a calculation becomes simple.

Figure 1D:
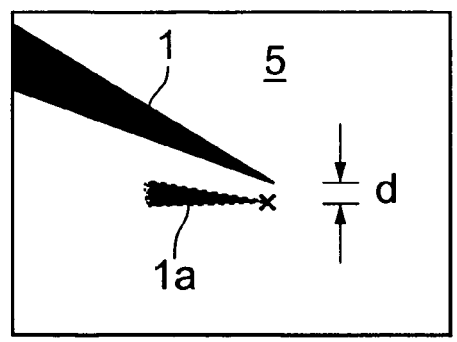
Figure 3:
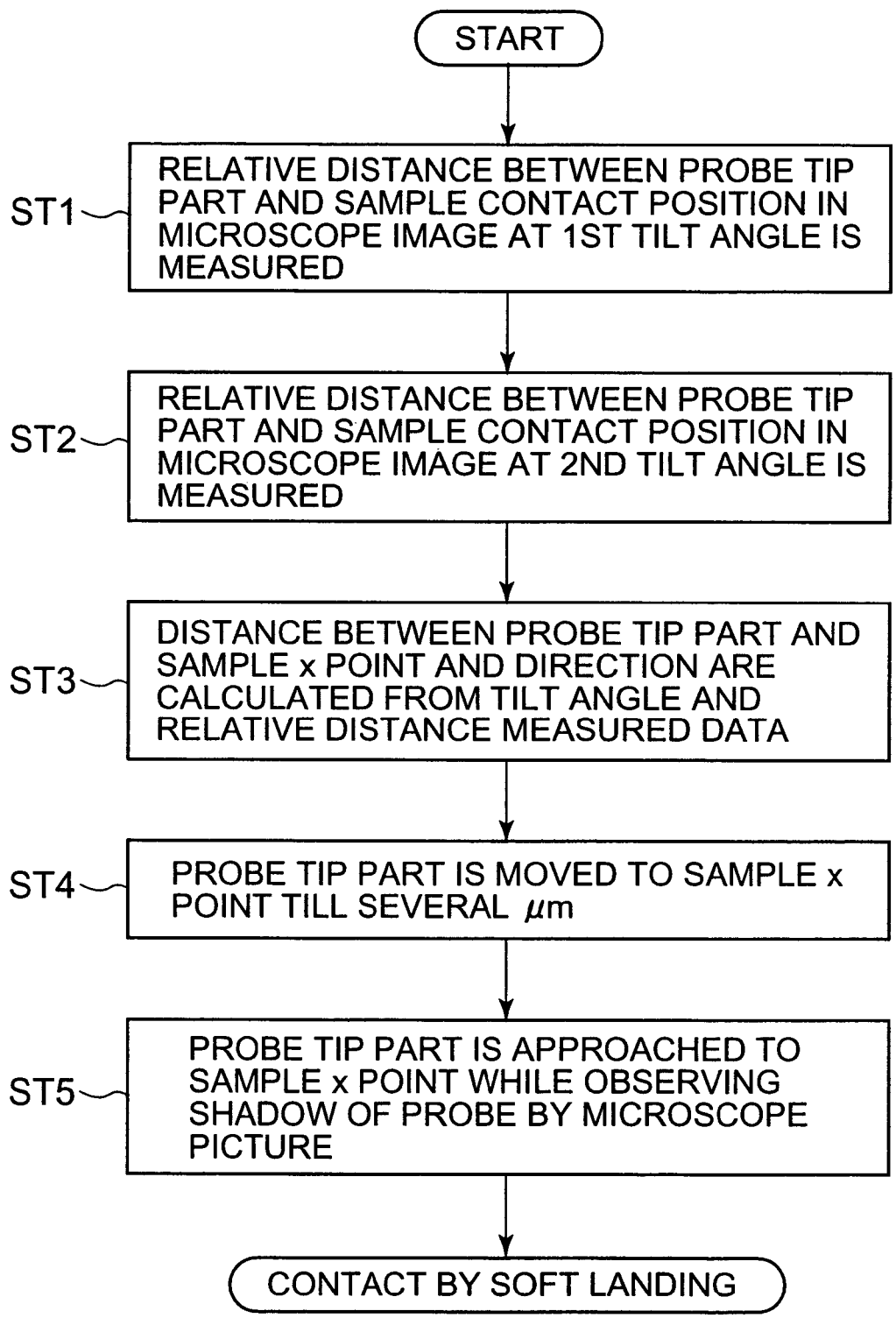
FIG. 3 is a flowchart explaining implementation procedures of the method according to the present invention.

Next, the probe approach procedure of the present invention is explained by referring to a flow chart shown in FIG. 3. In a eucentric position in which height positions of a tilt axis 6 of the sample stage 4 and the surface of the sample 5 are coincided with the same height by a controlling mechanism of a stage height (z-axis) such that no center sample position on the picture deviates even if the sample stage is tilted, Step 1) a 1st tilt angle is set, the microscope picture is photographed, and the relative distance between the tip part of the probe 1 and the position x of the sample to be contacted is measured. On this occasion, on the microscope image plane (tilt angle 0°) in which a charged particle beam has been irradiated from a sample surface vertical direction, if the sample position x to be contacted and the tip part position of the probe 1 are position-coincided, since it follows that the tip part of the probe 1 exists in a sample face vertical direction position from the sample position x to be contacted as shown in FIGS. 1A-1B, a calculation processing is simple, but it is not an indispensable condition. Step 2) Next, the relative distance between the sample position x to be contacted and the tip part position of the probe 1 in the microscope image photographed with the sample stage being set to a 2nd tilt angle is measured. Step 3) Here, from a relative distance data $d_1$ and the above tilt angle $\alpha_1$ in the picture at the 1st tilt angle and a relative distance data $d_2$ and the above tilt angle $\alpha_2$ in the picture at the 2nd tilt angle, a positional relation (distance and direction) between both is calculated. Step 4) Next, if the probe 1 is moved in a sample contact position x direction by for a value obtained by subtracting several μm from a value of this distance, a distance from the probe tip to the sample face becomes several microns or less. Through the above procedures, the probe is approached till a position in which its shadow can be observed. Step 5) If microscope-observed under a state of the distance capable of observing the shadow, as shown in FIG. 1D, since the probe 1 and its shadow 1a are being depicted on the sample 5 face, there is implemented a 2nd approach that is most characteristic in the present invention, in which it is gradually moved till tip parts of the probe 1 and the shadow 1a of the probe coincide while observing their microscope pictures, and it is possible to cause the probe 1 to softly contact the sample position x.

Embodiment 1

Figure 4A:
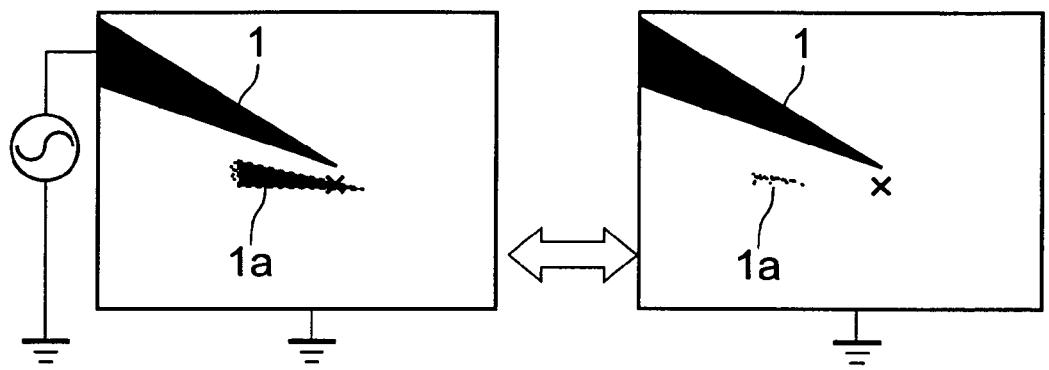
FIGS. 4A-4B are figures explaining an operation-effect in one embodiment of the present invention.
Figure 4B:
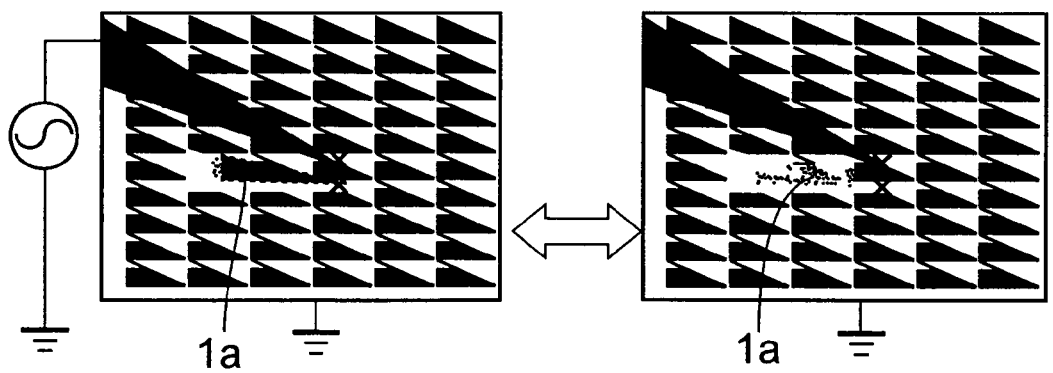
Figure 5:
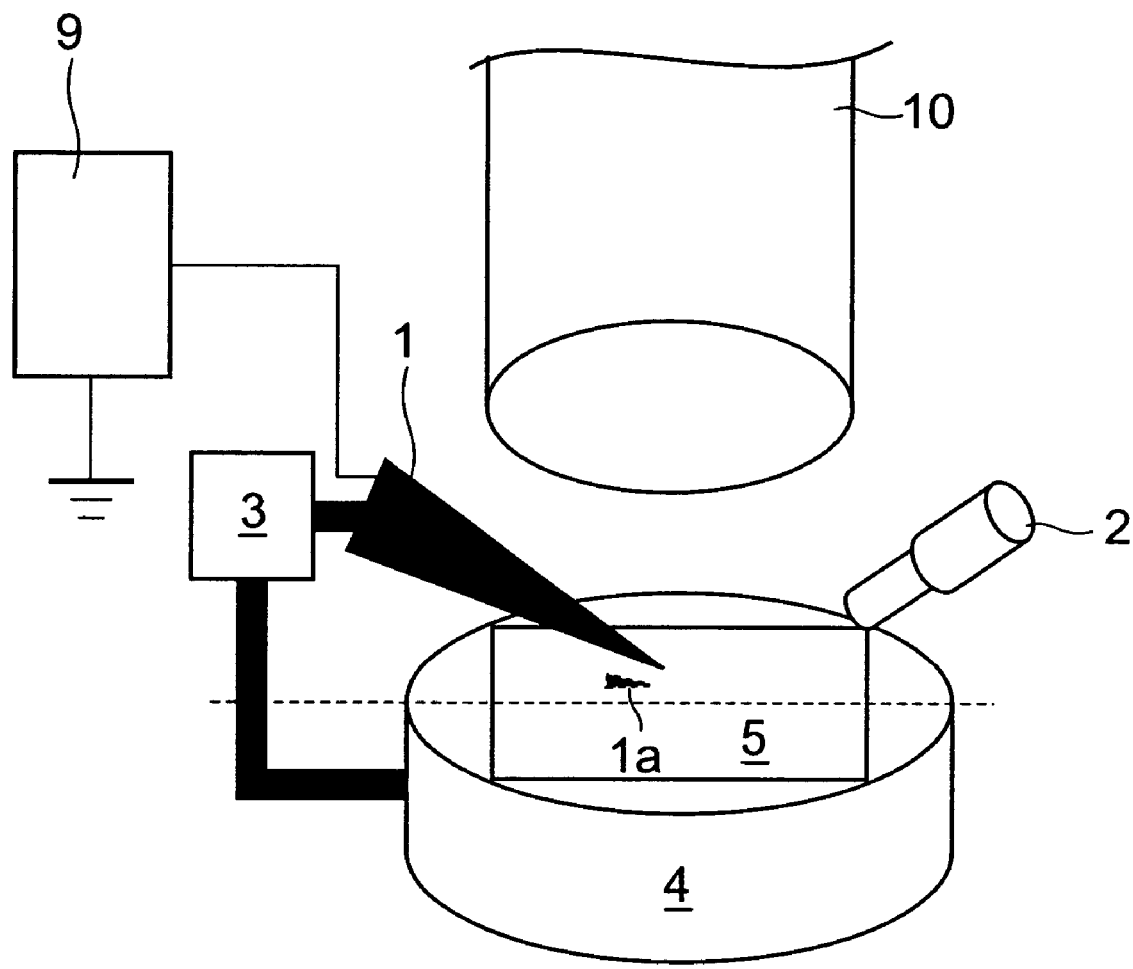
FIG. 5 is a figure explaining a constitution of one embodiment of the present invention.
Figure 6:
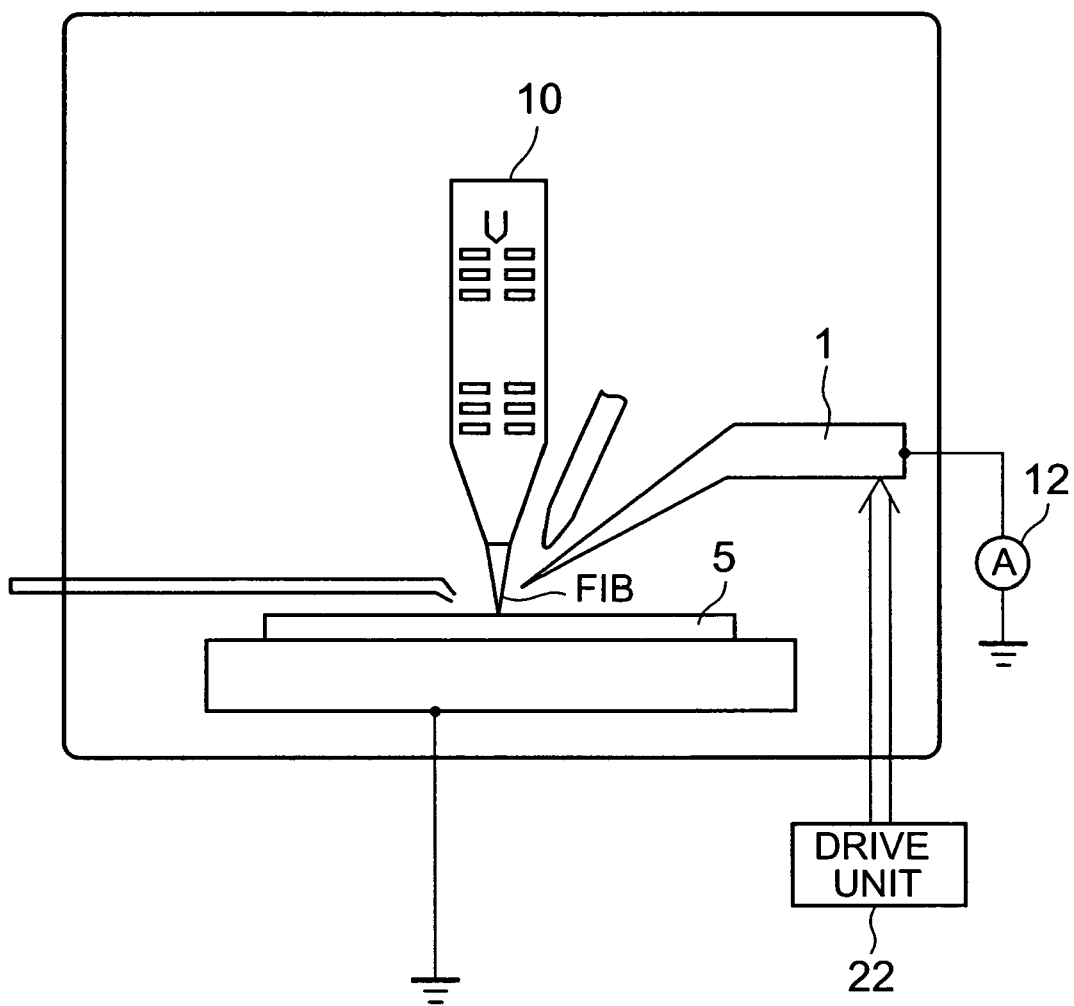
FIG. 6 is a figure explaining an example of a conventional FIB apparatus which detects a conventional contact between a probe and a sample.

Next, one embodiment of the present invention is shown in FIG. 5. As an apparatus, a variable voltage source 9 is connected to the electrically conductive probe 1, and there is outputted a voltage change whose period nt+t' (n is a natural number of 1 or more, t'<t) is far longer than a period t of scan picture one frame as the microscope of the charged particle beam. As shown in FIG. 4A, although the present invention is one performing the approach while monitoring the shadow 1a, of the probe 1, appearing in the microscope picture, in a case where a pattern resembling the probe tip exists in such a sample face as shown in FIG. 4B, there is a case where it becomes difficult to catch the shadow 1a of the probe 1 within the microscope picture. This embodiment is one adapted such that, by changing an electric potential of the probe 1, there is changed a rate at which secondary charged particles radiated from the sample face reach to a secondary charged particle detector 2. This is one in which the rate at which secondary charged particles radiated from the sample face by the beam irradiation reach to the secondary charged particle detector 2 is changed by such a phenomenon that the secondary charged particles radiated from the sample face are promoted/suppressed or the radiated secondary particles are attracted/repelled by the fact that an electric field strength made by the probe existing near the sample changes. On the microscope picture, this change appears as a luminance change of the shadow of the probe. Whereupon, in the present embodiment, it is suitable that this luminance change has a period liable to be recognized by eyes of a person who performs the microscope observation. For this reason, it is one constituted such that the voltage change whose period is far slower than one frame period of the charged particle beam is caused to be outputted, and this change is not always necessary to be a sine wave and may be a pulse-like voltage change such that the shade blinks for instance. However, it is a necessary condition that it is a change which is easy to be recognized by the eyes of the person as a luminous change.

In FIG. 4A, although there is shown a change of the shadow 1a in the sample whose surface is flat, a left image is a picture in which the shadow has been clearly depicted, and a right image is a figure in which the shadow has become faint. Since this luminance changes moment by moment in accordance with a change of the variable voltage source 9, it is easy that a worker discriminates an existence position of the shadow and performs an approach work. Even in a case of approaching to a substrate shape in which such a pattern liable to be confounded with the probe tip part as shown in FIG. 4B exists in the sample surface or onto a substrate in which an electrical insulator is mixed, since it changes moment by moment between the left picture in which the shadow has been clearly depicted and the right figure in which the shadow has become faint, it is easy to discriminate the confounding pattern and the shadow of the probe. Like this, the approach can be performed such that, while observing the microscope picture, the probe certainly and softly contact to the minute sample.

Further in a case where the electrically conductive probe and insulator are observed at the same time, the luminance of each is largely different, so that it is difficult to display their shape the same time within a gradation sequence of the display, and their contours blur. But it is possible to approach the probe safely by applying an arbitrary constant voltage to the probe since contrast among the probe, a shadow of the probe and the sample is adjusted such that the surface shape of the sample and the contour shape of the probe are clearly observed at the same time.

What is claimed is:

1. A method of approaching a probe comprising the steps of:
    approaching a tip of a probe to a target position on a sample mounted on a sample stage that is tilted at a preselected tilt angle about a tilt axis of the sample stage;
    observing with a charged particle beam microscope a distance between the tip of the probe and the target position of the sample while approaching the tip of the probe to the target position on the sample; and
    moving the probe in a direction so that on a display of the charged particle beam microscope, the tip of the probe and the tip of a shadow of the probe on the sample coincide at the target position on the sample.

2. A method of approaching a probe according to claim 1; wherein, in the moving step, the probe is moved until the tip of the probe and the tip of the shadow of the probe coincide to contact one another.

3. A method of approaching a probe according to claim 1; further comprising calculating a direction and an actual distance between the tip of the probe and the target position on the sample from relative distance values measured in plural microscope images photographed at two or more different known tilt angles of the sample stage and the preselected tilt angle of the sample stage.

4. A method of approaching a probe, comprising the steps of:
    providing a sample stage that is tiltable about a tilt axis and that has a sample mounted thereon;
    aligning a tip portion of a probe at a target position on a surface of the sample to be contacted on a microscope image obtained by irradiating a charged particle beam from a vertical position to a surface of the sample under a state that the tilt axis of the sample stage and a height position of the sample surface coincide;

measuring a relative distance between the target position on the sample surface to be contacted and the tip portion of the probe on a microscope image obtained with the sample stage tilted by a predetermined tilt angle;

calculating an actual distance between the target position on the sample surface and the tip portion of the probe from the calculated relative distance and the predetermined tilt angle;

linearly moving the probe toward the target position on the sample surface until the actual distance between the target position on the sample surface and the tip portion of the probe becomes several microns; and moving the probe toward the target position on the sample surface until the tip portion of the probe and the tip of a shadow of the probe on the sample surface coincide at the target position on the sample surface.

5. A method of approaching a probe according to claim 1; further comprising applying to the probe a fluctuating voltage so that a quantity of second electrons and ions detected while observing with the charged particle beam microscope is changed to thereby change a luminance of the shadow of the probe.

6. A method of approaching a probe according to claim 1; further comprising applying to the probe an arbitrary voltage so that a quantity of second electrons and ions detected while observing with the charged particle beam microscope is changed to thereby change a luminance of the shadow of the probe and control a luminance ratio between the sample and the shadow of the probe.

7. A charged particle beam apparatus having a microscope function, the charged particle beam apparatus comprising: a micro-manipulator; a probe formed of an electrically conductive material connected to a tip part of the micro-manipulator; a sample stage fixed to the micro-manipulator, the stage having at least four axes of movement including X, Y, Z axes and a tilt axis and being tiltable to a preselected tilt angle about the tilt axis; and variable voltage supplying means for supplying a variable voltage to the probe.

8. A method of approaching a probe according to claim 1; wherein the tilt axis of the sample stage is disposed parallel to a surface of the stage on which the sample is mounted.

9. A charged particle beam apparatus according to claim 7; wherein the tilt axis extends parallel to the X axis.

10. A charged particle beam apparatus according to claim 7; wherein the tilt axis of the sample stage is disposed parallel to a surface of the sample stage on which the sample is mounted.

11. A method of approaching a probe, comprising the steps of:

providing a sample stage that supports a sample and is mounted to undergo tilting movement about a tilt axis, a probe mounted to undergo movement relative to a target position on a surface of the sample, and a microscope for observing movement of the probe; and moving the probe in a direction in which a tip of the probe and a tip of a shadow of the probe on the sample surface coincide at the target position while observing with the microscope a distance between the tip of the probe and the target position and while the sample stage is tilted at a preselected tilt angle about the tilt axis.

12. A method according to claim 11; wherein the tilt axis of the sample stage is disposed parallel to a surface of the sample stage on which the sample is mounted.

13. A method according to claim 11; wherein the microscope is a charged particle beam microscope.

14. A method according to claim 11; wherein the probe is moved until the tip of the probe and the tip of the shadow of the probe coincide to contact one another.

15. A method according to claim 11; further comprising calculating a direction and an actual distance between the tip of the probe and the target position from relative distance values measured in plural microscope images photographed at two or more different tilt angles of the sample stage.

* * * * *